United States Patent [19]

Hesse

[11] Patent Number: Plant 6,838

[45] Date of Patent: Jun. 6, 1989

[54] CHRYSANTHEMUM PLANT NAMED CINDY

[75] Inventor: Peter S. Hesse, Bradenton, Fla.

[73] Assignee: Ball Seed Company, W. Chicago, Ill.

[21] Appl. No.: 150,067

[22] Filed: Jan. 29, 1988

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Cindy having very small lavender-pink flowers, with the immature, unexpanded ray florets appearing as a darker lavender eye; very freely branching, ten week flower response, and excellent performance under low light, cool weather conditions.

1 Drawing Sheet

The present invention comprises a new and distinct cultivar of *Dendranthema grandiflora,* commonly referred to as Chrysanthemum and hereinafter referred to by the cultivar name Cindy.

Cindy is a product of a planned breeding program which had the objective of creating new Chrysanthemum cultivars with an abundance of small lavender-pink flowers, excellent performance when grown under dark cool conditions, and compact growth habit, thereby making it ideally suited for use in pot mum programs. Such traits in combination were not present or needed improvement in previously available commercial cultivars.

Cindy was originated from a hybridization made by applicant in a controlled breeding program in Parrish, Fla. in 1984. The female parent was Excel, disclosed in U.S. Plant Pat. No. 5,495. The male parent of Cindy was Bingo, disclosed in U.S. Plant Pat. No. 5,972. Cindy was discovered and selected as one flowering plant within the progeny of the stated parentage by applicant on Dec. 30, 1984 in a controlled environment in Parrish, Fla.

The first act of asexual reproduction of Cindy was accomplished when vegetative cuttings were taken from the initial selection in February, 1985 in a controlled environment in Parrish, Fla. by a technician working under formulations established and supervised by applicant. Horticultural examination of selected units initiated in November, 1985 has demonstrated that the combination of characteristics as herein disclosed for Cindy are firmly fixed and are retained through successive generations of asexual reproduction.

Cindy has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Cindy, which in combination distinguish this Chrysanthemum as a new and distinct cultivar:

1. Ten (10) week flower response.
2. Very small flowers (3–4 cm in diameter).
3. Lavender-pink ray floret color. Immature, unexpanded ray florets are darker than the mature, fully expanded ray florets giving the flower the appearance of a "dark eye".
4. Very freely branching.
5. Individual ray florets 8–20 mm in length and 4–7 mm in width.
6. Not suitable for production during periods of warm weather. At temperatures above 80° F., Cindy develops bracts in the center of the flower.
7. Performs extremely well under low light, cool weather conditions.
8. Medium green, small foliage.

Of the many commercial cultivars known to the present inventor, the most similar in comparison to Cindy is the maternal parent Excel. In comparison to Excel, Cindy has a two week later flower response, a more vigorous growth habit, lavender-pink flower color, and is a better performer under low light, cool weather conditions. The decorative flower form and small flower size of Cindy are similar to those same characteristics of Excel.

The accompanying photographic drawing shows typical inflorescence and foliage characteristics of Cindy, with colors being as nearly true as possible with illustrations of this type. The photograph is in black and white, with a few flowers being colored to accurately depict true flower color.

In the following description, color references are made to The Royal Horticultural Society Colour Chart. The color values were determined between 2:15 and 2:30 p.m. on Jan. 5, 1988 under fluorescent light at Parrish, Fla.

Classification:

*Botanical.*—*Dendranthema grandiflora,* cv. Cindy.

*Commercial.*—Decorative pot mum.

INFLORESCENCE

A. Capitulum:

*Form.*—Flat.

*Type.*—Double.

*Diameter across face.*—3–4 cm.

B. Corolla of ray florets:

*Color (general tonality from a distance of three meters).*—Lavender-pink.

*Color* (*upper surface*).—Immature, unexpanded ray florets are 77B; mature, fully expanded ray florets are 75B.

*Color* (*under surface*).—75D.

C. Corolla of disc florets:

*Color* (*mature*).—Yellow.

*Color* (*immature*).—Yellow-green.

D. Reproductive organs:

*Androecium.*—Present in disc florets only.

*Gynoecium.*—Present in both disc and ray florets.

PLANT

A. General appearance:

*Height.*—29 cm above the edge of the pot; height may vary depending upon growing conditions and cultural practices.

B. Foliage:

*Color* (*upper surface*).—137A.

*Color* (*under surface*).—138B.

*Shape.*—Ovate, deeply lobed with crenate margins.

I claim:

1. A new and distinct cultivar of Chrysanthemum plant named Cindy, as illustrated and described, and parts thereof.

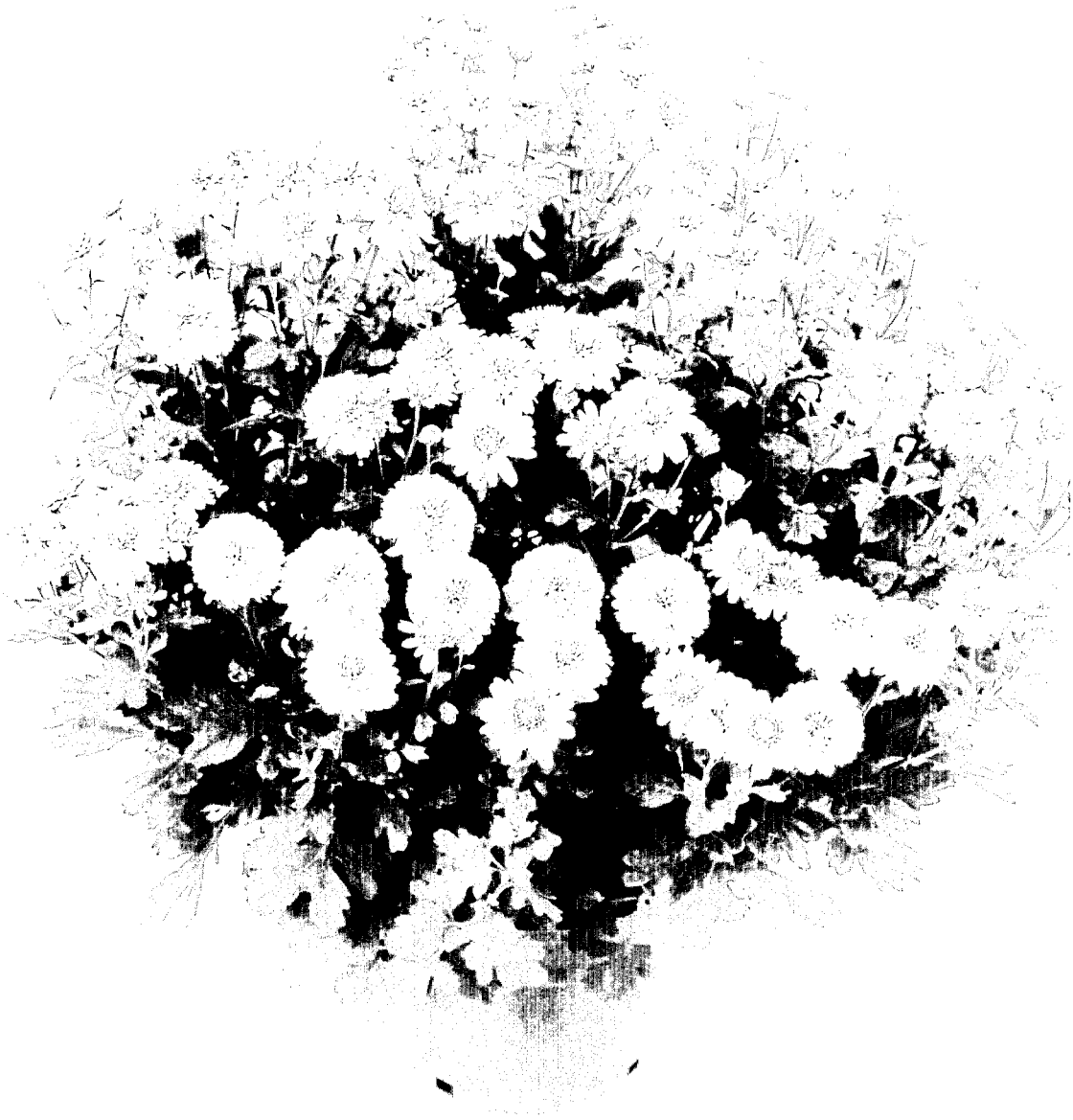

* * * * *